United States Patent [19]

Ono et al.

[11] 4,365,089

[45] Dec. 21, 1982

[54] SYNTHESIS OF UREA

[75] Inventors: Hiroshi Ono, Fujisawa; Hidetsugu Fujii, Mobara; Shigeru Inoue, Kamakura, all of Japan

[73] Assignee: Mitsui Toatsu Chemicals, Inc., Tokyo, Japan

[21] Appl. No.: 293,926

[22] Filed: Aug. 18, 1981

[30] Foreign Application Priority Data

Sep. 5, 1980 [JP] Japan ............................... 55/122328

[51] Int. Cl.³ .......................................... C07C 126/02
[52] U.S. Cl. ........................................................ 564/67
[58] Field of Search ............................................ 564/67

[56] References Cited

U.S. PATENT DOCUMENTS

| 2,056,283 | 10/1936 | Lawrence et al. | 564/67 |
| 3,005,849 | 10/1961 | Otsuka | 564/67 |
| 3,146,263 | 8/1964 | Otsuka | 564/67 |
| 3,356,723 | 12/1967 | Kaasenbrood | 260/555 |
| 4,301,299 | 11/1981 | Inoue et al. | 564/67 |

FOREIGN PATENT DOCUMENTS

| 38-19964 | 9/1963 | Japan | 564/67 |
| 45-41372 | 12/1970 | Japan | 564/67 |
| 46-11009 | 3/1971 | Japan | 564/67 |
| 51-75022 | 6/1976 | Japan | 564/67 |
| 54-90118 | 7/1979 | Japan | 564/67 |
| 7713190 | 11/1977 | Netherlands | 564/67 |
| 1047954 | 11/1966 | United Kingdom | 564/67 |
| 1185944 | 3/1970 | United Kingdom | 564/67 |

*Primary Examiner*—John Doll
*Attorney, Agent, or Firm*—Fisher, Christen & Sabol

[57] ABSTRACT

The specification describes a process for synthesizing urea. The process comprises reacting ammonia and carbon dioxide in a molar ratio of 3:1–5:1 and at a pressure of 150–250 Kg/cm²G, subjecting the resultant reaction mixture to a stripping step using gaseous carbon dioxide at a pressure substantially equal to the urea synthesis pressure and a temperature of 195°–210° C. to remove unreacted ammonia and unreacted carbon dioxide contained in the reaction mixture so that the content of unreacted ammonia is lowered to 10–15% by weight. This invention ensures a high conversion ratio from carbon dioxide to urea, considerably little formation of biuret during the stripping step, and reduced consumption of high pressure steam.

5 Claims, 1 Drawing Figure

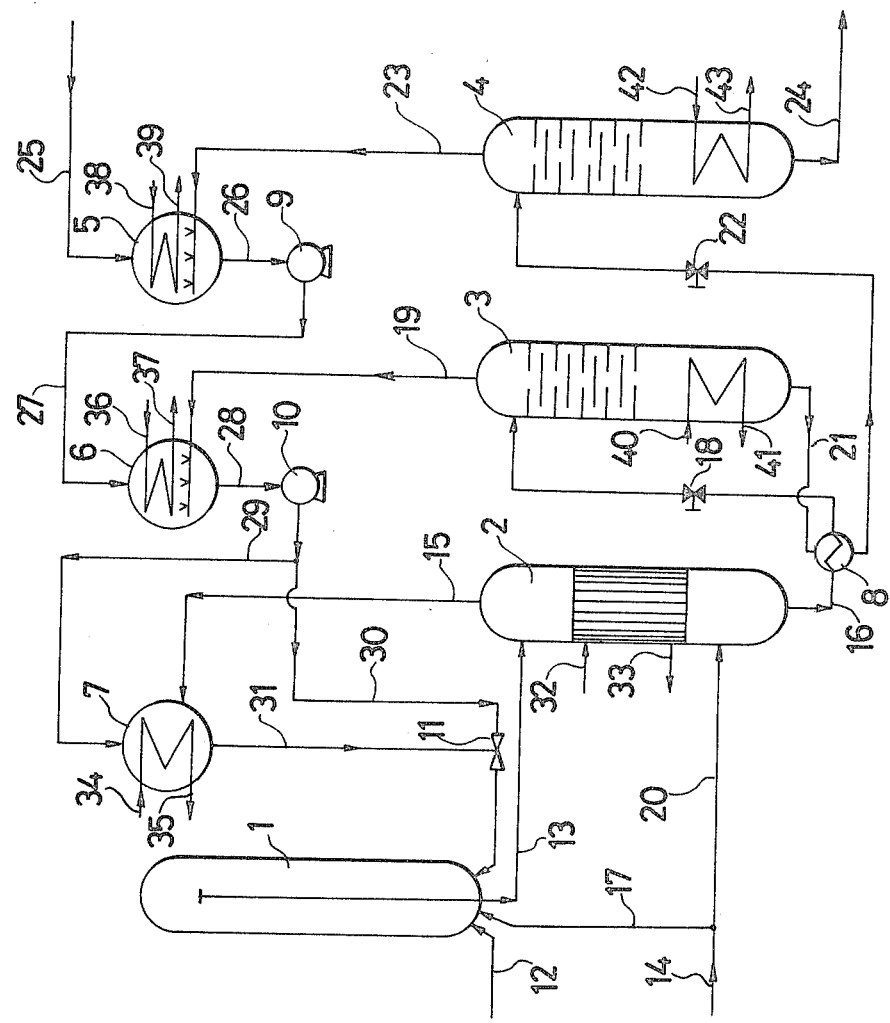

SYNTHESIS OF UREA

BACKGROUND OF THE INVENTION (a) Field of the Invention

This invention relates to an improved cyclic process for the synthesis of urea. More particularly, it relates to an improvement in or relating to a process for subjecting a urea synthesis effluent, which has been obtained by reacting ammonia and carbon dioxide at a urea synthesis temperature and pressure and contains urea, water, unreacted ammonia and unreacted carbon dioxide, to a stripping step using carbon dioxide at a pressure substantially equal to the urea synthesis pressure.

(b) Description of the Prior Art

As one of conventional methods for separating and recovering unreacted ammonia and unreacted carbon dioxide from a urea synthesis effluent obtained in a urea synthesis step, there is known a method in which the urea synthesis effluent is subjected to a stripping step using one of the raw materials, namely, carbon dioxide, at a pressure substantially equal to the urea synthesis pressure, and a separated gaseous mixture of unreacted ammonia and unreacted carbon dioxide is then condensed and recycled to the urea synthesis step (See, for example, Japanese Patent Publication No. 19964/1963). According to this method, the separation of unreacted ammonia and unreacted carbon dioxide is carried out at a pressure substantially equal to the urea synthesis pressure. Thus, this particular method is advantageous in that the condensation heat given off upon recovering the thus-separated unreacted ammonia and carbon dioxide by condensing the same can be recovered at a relatively high temperature level in the form of steam or the like. However, this method is accompanied by some drawbacks which are described below.

First of all, it has been reported that the above method does not allow to increase the $NH_3/CO_2$ molar ratio in a urea synthesis step so as to achieve a high degree of the stripping effect by carbon dioxide. According to the aforementioned Japanese Patent Publication No. 19964/1963, it is said to be necessary to select as the $NH_3/CO_2$ molar ratio in the urea synthesis step a value not too much apart from 2.0, namely, a value in the range of from 1.5 to 3.5. Example 1, which appears to be the most preferable embodiment, recites about 2.5 as the $NH_3/CO_2$ molar ratio.

However, if a value close to 2 is chosen as the $NH_3/CO_2$ molar ratio in a urea synthesis step, the conversion ratio of carbon dioxide to urea declines. For example, where the temperature and $H_2O/CO_2$ molar ratio as a urea synthesis conditions are respectively 185° C. and 0.3, the conversion ratio of carbon dioxide to urea at equilibrium is about 62.5% if the $NH_3/CO_2$ molar ratio is 2.5 whereas it increases to 76.9% if the same molar ratio is 4.0. As a result, a considerably great difference arises in that the former $NH_3/CO_2$ molar ratio requires a decomposition and separation of unreacted ammonium carbamate in the amount of 0.78 ton per ton of urea to be produced whereas the latter $NH_3/CO_2$ molar ratio needs a decomposition and separation of unreacted ammonium carbamate whose quantity is only one half of the unreacted ammonium carbamate resulting from the use of the former $NH_3/CO_2$ molar ratio, in other words, 0.39 ton per ton of urea to be produced. Needless to say, the thermal energy required for the production of urea is not limited to that required for the decomposition and separation of such unreacted ammonium carbamate but includes that needed for the separation of unreacted free ammonia. However, the latter thermal energy is little, compared with the former one. Thus, in a stripping step using carbon dioxide which step requires carrying out the synthesis of urea with such a low $NH_3/CO_2$ molar ratio that the thermal energy required for the decomposition of unreacted ammonium carbamate tends to become great inevitably. Although a considerable part of the thermal energy used for the decomposition and separation of such unreacted ammonium carbamate can be recovered as low pressure steam in the condensation step of separated ammonia and carbon dioxide, it results in a situation where highly valuable high pressure steam is consumed in great quantity and, instead, low pressure steam of a low value is produced.

Secondly, when a urea synthesis effluent obtained under such a low $NH_3/CO_2$ molar ratio condition is subjected to a stripping step using carbon dioxide, the molar ratio of unreacted $NH_3$ to unreacted $CO_2$ remaining in a resultant urea solution is generally very small, more specifically, becomes a value close or substantially equal to 2.

The present inventors found that, where the concentration of unreacted carbon dioxide remaining in a urea solution is so high compared with that of unreacted ammonia also remaining in the same urea solution that the $NH_3/CO_2$ molar ratio falls below 2.5, an exposure of the urea solution to a temperature of 190° C. or higher will result in considerable increment in the hydrolysis of urea, which is not advantageous to the process, and the formation of biuret, which are undesirable from the viewpoint of urea quality, compared with a urea solution containing unreacted carbon dioxide in a lower concentration.

In the conventional art, as disclosed in Japanese Patent Laid-Open Publication No. 90118/1979, a method has been adopted to solve the above-described drawbacks in which a urea solution obtained by subjecting a urea synthesis effluent to a stripping step using carbon dioxide is rapidly cooled to 155°–175° C. Although this method seems to be effective in suppressing the hydrolysis of urea and the formation of biuret, it should be used with enlarged apparatus, which is adapted to conduct a stripping step using carbon dioxide therein. Also, equipment is needed to adjust the temperature of carbon dioxide to be used for the stripping to 80°–125° C. Since the temperature of $CO_2$ gas discharged from a carbon dioxide gas compressor used in a urea synthesis process generally ranges from 140° to 180° C., a carbon dioxide gas cooler operable under high pressure (urea synthesis pressure) is required to follow the above recommendation, causing another disadvantage that carbon dioxide gas of a high temperature is cooled and its heat is taken out of the system.

SUMMARY OF THE INVENTION

An object of this invention is to provide a process capable of synthesizing urea with a high conversion ratio from carbon dioxide to urea.

Another object of this invention is to provide a process for synthesizing urea in which the hydrolysis of urea and formation of biuret are considerably reduced upon stripping unreacted ammonia and unreacted carbon dioxide by using carbon dioxide.

A further object of this invention is to provide a process for synthesizing urea, which process consumes a lesser amount of high pressure steam.

Accordingly, the present invention provides the following process for the synthesis of urea: a process for the synthesis of urea comprising reacting ammonia and carbon dioxide in a molar ratio of 3:1–5:1 at a urea synthesis pressure of 150–250 Kg/cm$^2$G to obtain a urea synthesis effluent containing urea, water, unreacted ammonia and unreacted carbon dioxide, and subjecting the urea synthesis effluent to a stripping step using carbon dioxide at a pressure substantially equal to the urea synthesis pressure and at a temperature of 195°–210° C. to separate unreacted ammonia and unreacted carbon dioxide, thereby obtaining a urea solution containing 10–15% by weight of unreacted ammonia.

The urea solution from the stripping step may then be subjected to a separation step at a pressure of 10–30 Kg/cm$^2$G and at a temperature of 150°–170° C. to further separate unreacted ammonia and unreacted carbon dioxide and to obtain a urea solution containing unreacted ammonia in a proportion of 8% by weight or less. The thus-obtained urea solution may thereafter be subjected to a separation step of unreacted ammonia and unreacted carbon dioxide at a pressure lower than that employed in the above separation step, thereby obtaining a urea solution substantially free of unreacted ammonia and unreacted carbon dioxide.

BRIEF DESCRIPTION OF THE DRAWING

The appended single drawing is a flow sheet for use in describing one embodiment according to this invention.

DETAILED DESCRIPTION OF THE INVENTION

The present invention found the following four facts on which the present invention was completed.

(1) Even if the NH$_3$/CO$_2$ molar ratio in the synthesis of urea is relatively high, namely, 3.5–5.0, it may be easy to conduct a further CO$_2$ stripping step with respect to a urea solution which has been obtained by subjecting a urea synthesis effluent to a stripping step using carbon dioxide at urea synthesis pressure to remove unreacted ammonia and unreacted carbon dioxide from the effluent so long as the concentration of unreacted NH$_3$ remaining in the urea solution is 10–15% by weight;

(2) In a urea solution obtained by subjecting a urea synthesis effluent to a stripping step using carbon dioxide as mentioned above, the molar ratio of unreacted ammonia to unreacted carbon dioxide, both remaining in the urea solution, is as high as 3–3.5. Under such conditions, even if the stripping step using CO$_2$ is carried out at a high temperature of 195°–210° C. which is considered to be too high for conventional stripping methods, the hydrolysis of urea and formation of biuret are considerably limited compared with reaction conditions in which the above-mentioned molar ratio is not higher than 2.5, thereby making it unnecessary to adopt special means for inhibiting or minimizing such hydrolysis and formation;

(3) If the stripping step using carbon dioxide can be performed at such a high temperature, it would become feasible to adopt a high pressure of 150–250 Kg/cm$^2$G as the stripping pressure (in other words, the urea synthesis pressure). Such a high pressure increases the conversion ratio of carbon dioxide to urea in a urea synthesis step. Furthermore, it permits condensation, at a high temperature, of ammonia and carbon dioxide gases separated from the stripping step using carbon dioxide, thereby allowing the recovery of excessive heat in the form of high pressure steam; and (4) It is preferable to separate unreacted ammonia and unreacted carbon dioxide remaining in the thus-obtained urea solution which contains 10–15% by weight of unreacted ammonia in a second separation zone for unreacted materials which zone is maintained at a pressure of 10–30 Kg/cm$^2$G and a temperature of 150°–170° C. In this pressure range, the whole amount of ammonia and carbon dioxide to be separated can be readily condensed or absorbed in an absorbent at a temperature of 90°–120° C. The condensation or absorption heat to be given off is within a temperature range of 90°–120° C. and thus may be effectively used for condensing a urea solution in vacuo or preheating liquefied NH$_3$ used for the synthesis of urea.

In the above-described second separation zone for unreacted materials, it is necessary to lower the concentration of unreacted NH$_3$ remaining in the urea solution to a level of 8% by weight or lower. This facilitates the separation of unreacted ammonia and unreacted carbon dioxide in a subsequent separation zone for unreacted materials, which zone is operated at a low pressure of 1–5 Kg/cm$^2$G, as well as the condensation of thus-separated ammonia and carbon dioxide gases at the same low pressure or absorption of the same gases in water, aqueous urea solution or aqueous dilute ammonium carbonate solution. Such a low NH$_3$ concentration is also of importance in reducing in quantity water which accompanies the ammonia and carbon dioxide to be recycled to the urea synthesis step after they have been condensed or absorbed.

In practicing the present invention, it is necessary to control the NH$_3$/CO$_2$ molar ratio during the urea synthesis step within 3.0–5.0. As the NH$_3$/CO$_2$ molar ratio becomes smaller, more unreacted carbon dioxide tends to remain in a urea solution to be obtained from the stripping step and the conversion ratio of carbon dioxide to urea in the urea synthesis step decreases, thereby failing to fulfill the above-described objects of this invention. The lower limit of the NH$_3$/CO$_2$ molar ratio is determined by a molar ratio which brings about the effects of this invention clearly. It is about 3.0 but, preferably, 3.5 or higher.

On the other hand, there is no specific critical point with respect to the upper limit of the NH$_3$/CO$_2$ molar ratio. However, if it exceeds 5.0, it becomes necessary to raise the temperature of the stripping step to at least 210° C. Such a high temperature is not considered to be suitable to materials which make up the stripping apparatus. This disadvantage may be compensated by reducing the pressure in the stripping step. However, this means the use of a reduced pressure in the urea synthesis step, adversely affecting the economy of the overall process. For the reasons mentioned above, the NH$_3$/CO$_2$ molar ratio employed in the urea synthesis zone for practicing the invention may be 3.0–5.0, and more preferably, 3.5–5.0.

It is necessary to adopt at least 180° C. as the temperature of the urea synthesis step in order to achieve an industrially meritorious reaction velocity under the condition of such an NH$_3$/CO$_2$ molar ratio. From the economical point of view, 185° C. or a higher temperature is preferred. The upper limit of the urea synthesis temperature may be set at 200° C. in view of temperature limitations of the materials making up the apparatus, a fact that the conversion ratio of carbon dioxide to urea decreases beyond 200° C., etc.

As a pressure in the urea synthesis zone, there is employed a pressure higher than a urea synthesis equilibrium pressure which is determined from such an $NH_3/CO_2$ molar ratio and reaction temperature. In the process of this invention, a pressure in the range of from 150 to 250 $Kg/cm^2G$ is employed.

Under the urea synthesis pressure as described above, it is necessary to use a temperature of from 195° to 210° C. to obtain in a stripping step a urea solution containing 10–15% by weight of unreacted ammonia.

As there are such close relationship as described above among $NH_3/CO_2$ molar ratio, reaction temperature, reaction pressure (in other words, the pressure in the stripping step) and stripping temperature, none of the above process conditions shall exceed their respective ranges.

In this invention, it may be possible to reduce in quantity carbon dioxide and water contained in a gaseous mixture of ammonia and carbon dioxide to be separated in the second separation zone for unreacted materials, by first adjusting the temperature of a urea solution resulting from the stripping step using carbon dioxide and containing 10–15% by weight of unreacted ammonia to 180°–195° C. and then supplying the thus temperature-adjusted urea solution to the second separation zone. This brings about preferable results, which will be described hereinbelow.

Namely, the separation of ammonia takes place with priority in the second separation zone for unreacted materials and, as a result the separation of carbon dioxide and water is reduced there. This, in turn, leads to the following two favorable results.

Firstly, in the second separation zone for unreacted materials, ammonia which requires a small heat quantity for the separation is preferentially separated at a relatively high pressure of 10–30 $Kg/cm^2G$. Carbon dioxide which requires a large heat quantity for the sepration principally remains in the solution in the second separation zone but is separated in a subsequent low pressure separation zone for unreacted materials. Thus, a preferred result has been brought about that, to obtain a urea solution containing the same quantity of remaining unreacted ammonia, the heat quantity required in the second separation zone, which requires steam of a high pressure of 10 $Kg/cm^2G$ or higher can be decreased although the heat quantity required in a low pressure separation zone, which can be operated by steam of a low pressure of 5 $Kg/cm^2G$ or lower have to be increased instead. Since this low pressure steam of 5 $Kg/cm^2G$ or less can be obtained when recovering heat given off upon condensing or absorbing ammonia and carbon dioxide gases which have been separated in the stripping step using carbon dioxide, both high pressure steam introduced into and low pressure steam discharged for the overall urea synthesis system will be reduced.

Secondly, by reducing the water content in the gaseous mixture separated from the second separation zone for unreacted materials, it is possible to reduce the quantity of water to be recycled to the urea synthesis zone. Thus, water which acts adversely on the conversion ratio of carbon dioxide to urea in a urea synthesis reaction is reduced in quantity, thereby achieving a high conversion ratio of carbon dioxide to urea.

As a method for adjusting the temperature of a urea solution supplied from the stripping step using carbon dioxide and containing 10–15% by weight of remaining unreacted ammonia, it is preferable, prior to supplying the urea solution to the second separation zone for unreacted materials, to cause the urea solution to contact with carbon dioxide gas as a stripping agent under adiabatic conditions or to subject the urea solution to a heat exchange with a urea solution of 150°–170° C. drawn out of the second separation zone for unreacted materials. It is not necessary to take the heat out of the system when such a method is adopted. Thus, there does not occur heat loss in the overall urea synthesis process, and, consequently, the economical advantage of the process is not sacrificed.

The effect of the above-described temperature adjustment can be observed when adjusted to a temperature below the stripping temperature of 195°–210° C. Thus, it is unnecessary to limit the thus-adjusted temperature within a specific range from its effect. However, taking into consideration that, when envisaging the overall urea synthesis process, the thus-adjusted temperature can be reached without losing heat, the heat load in the second separation zone must not be increased too much and the effect of the temperature adjustment must be clearly observed, it is preferable to adjust the temperature to a range of 175° to 210° C., especially 180°–195° C.

Moreover, the effect of the heat adjustment will be made more distinct where there is used a rectification column as shown in Japanese Patent Publication No. 20380/1965. Namely, by employing a rectification column, a temperature adjustment of a urea solution obtained from a stripping step results in a temperature adjustment of a gaseous mixture separated in the second separation zone for unreacted materials, whereby meeting the above-described objects of this invention.

The present invention brings about various effects, which will be summarized as follows:

(1) Owing to a high conversion ratio of carbon dioxide to urea, it is possible to reduce in quantity high pressure steam of 10 $Kg/cm^2G$ or higher to be introduced into the urea synthesis process;

(2) The hydrolysis of urea and formation of biuret are considerably restrained during the stripping step using carbon dioxide; and (3) It is possible to recover steam at a higher pressure in the urea synthesis process.

Now, an embodiment of this invention is described in accordance with the accompanying drawing.

In the drawing, a urea reactor 1 is supplied with ammonia through a line 12, a part of carbon dioxide through lines 14 and 17, and a solution containing recovered unreacted ammonia and unreacted carbon dioxide through an ejector 11. The urea reactor 1 is operated at a temperature of from 185° to 200° C. and a pressure in the range of from 150 to 250 $Kg/cm^2G$, while maintaining the $NH_3/CO_2$ molar ratio within 3 to 5.

A urea synthesis effluent obtained in the urea reactor 1 is supplied to a first separator 2 for the removal of unreacted materials through a line 13 and is brought into a counter-current contact in the form of falling films with carbon dioxide fed as a stripping agent from the bottom of the separator 2 via lines 14 and 20. Here, the first separator 2 is heated to a temperature of from 195° to 210° C. by steam of 20 $Kg/cm^2G$ which is charged through a line 32. The steam, which has been used to heat the first separator 2, is discharged through a line 33 in the form of steam condensate. The resulting urea solution containing 10–15% by weight of remaining unreacted ammonia is then fed through a line 16 to a heat exchanger 8, where its temperature is controlled to 180°–195° C. Thereafter, it is charged into a second separator 3 for the removal of unreacted materials through a reducing valve 18. On the other hand, unreacted ammonia and unreacted carbon dioxide separated from the urea synthesis effluent are drawn out of the first separator 2 from the top of same through a line 15 as a gaseous mixture together with a small amount of water and carbon dioxide which was used as the stripping agent.

The second separator 3 for the removal of unreacted materials is a rectification column comprising a number of shelves provided in an upper portion thereof as well as a heating unit having a steam line 40 and discharge line 41 for steam condensate, both lines disposed in a lower portion thereof. In the second separator 3, the concentration of unreacted ammonia remaining in the urea solution fed to the separator 3 is reduced to a level of 8% by weight or lower. Thereafter, the urea solution is fed back to the heat exchanger 8 through a line 21. A gaseous mixture of unreacted ammonia and unreacted carbon dioxide separated in the separator 3 is drawn out of the separator 3 from an upper portion thereof through a line 19. The temperature of the urea solution passed through the reducing valve 18 drops as parts of ammonia and carbon dioxide contained therein are released. Where the temperature of the urea solution is adjusted to 180°–195° C. by means of the heat exchanger 8, the urea solution passed through the reducing valve 18 will have a temperature in the range of 120°–140° C. The thus-obtained urea solution is brought into contact with the ascending separated gaseous mixture and cools it down while flowing down through the shelf portion of the second separator 3, thereby reducing the content of water contained in the gaseous mixture drawn out through the line 19. As shelves of the second separator 3, perforated plates or bubble caps are favorably employed. However, the shelves are not necessarily limited to such specific plates or bubble caps. Any means may be used as such shelves so long as it has a rectification effect. A packed layer may also be employed.

The urea solution fed to the heat exchanger 8 through line 21 is then charged into a low pressure separator 4 for the removal of unreacted materials, which separator 4 is operated at a pressure of 1–5 Kg/cm$^2$G and a temperature of 120°–160° C. Unreacted ammonia and unreacted carbon dioxide contained in the urea solution supplied to the separator 4 are removed in the separator 4 and a urea solution substantially free of unreacted ammonia and carbon dioxide is charged out through a line 24. A separated gaseous mixture is drawn out from the separator 4 through a line 23. Although the low pressure separator 4 may not be limited to any specific type, the chart illustrates a separator of the same type as the second separator 3. The separator 4 is provided at the lower portion thereof with lines 42 and 43 respectively for supplying steam and discharging steam condensate.

The gaseous mixture from the line 23 consists of ammonia, carbon dioxide and a small amount of water and is absorbed in a low pressure absorber 5 for unreacted materials by supplying to the absorber 5 an aqueous urea solution or an aqueous dilute ammonium carbonate solution. It is thus taken out from the separator 5 in the form of an aqueous solution through a line 26 and supplied to a second absorber 6 for unreacted materials through a pump 9 and line 27. In the meantime, heat generated by the absorption of the gaseous mixture is released outside the system via lines 38 and 39 through which coolant water flows.

To the second absorber 6, is also fed the gaseous mixture of ammonia, carbon dioxide and a small amount of water through the line 19. This gaseous mixture is absorbed in the aqueous solution supplied from the line 27. Heat generated by this absorption can be taken out of the second absorber 6, for example, by means of the aqueous urea solution which is introduced through a line 36 and discharged through a line 37 and may be used effectively for the concentration of the aqueous urea solution in vacuo.

The resulting aqueous solution, which contains ammonia, carbon dioxide and water, enters a pump 10 through a line 28 and is pressurized there. A part of the thus-pressurized aqueous solution is charged as an absorbent into a first absorber 7 for the removal of unreacted materials and the remainder is fed through a line 30 as a driving fluid for an ejector 11 which serves to recycle the solution obtained from the first absorber 7 to the urea reactor 1.

When a gaseous mixture of ammonia, carbon dioxide and water is fed to the first absorber 7 through a line 15 and absorbed there, heat is generated. This heat can be effectively recovered, for example, by heating boiler feed water by means of lines 34 and 35 and generating low pressure steam of 3–5 Kg/cm$^2$G.

The practice of this invention will be described more specifically, making reference to the following embodiment. However, this embodiment shall not be construed as limiting the present invention thereto.

EXAMPLE

To a urea synthesis apparatus whose outline is as shown in the accompanying drawing, were fed 28,340 kg/day of liquefied NH$_3$ through the line 12 and 36,670 kg/day of carbon dioxide through the line 14. Through the line 24, 71,360 kg/day of 69.8 wt.% aqueous urea solution containing a small amount of NH$_3$, CO$_2$ and biuret was charged out. In the above operation, the flow rates, compositions, temperatures and pressures in various steps of the process are as shown in Table I.

TABLE I

| Composition | Line | | | | | | | |
|---|---|---|---|---|---|---|---|---|
| | 12 | 13 | 14 | 15 | 16 | 17 | 19 | 20 |
| Urea (kg/day) | | 51,271 | | | 50,502 | | | |
| Ammonia (kg/day) | 28,340 | 51,539 | | 41,433 | 10,525 | | 4,920 | |
| Carbon dioxide (kg/day) | | 14,549 | 36,670 | 29,840 | 9,080 | 12,835 | 5,538 | 23,836 |
| Water (kg/day) | | 24,981 | | 2,988 | 21,774 | | 256 | |
| Biuret (kg/day) | | 128 | | | 162 | | | |
| Total | 28,340 | 142,468 | 36,670 | 74,261 | 92,043 | 12,835 | 10,714 | 23,836 |
| Temperature (°C.) | 35 | 190 | 140 | 192 | 198(182) | 140 | 136 | 140 |
| Pressure (kg/cm$^2$G) | 180 | 180 | 180 | 180 | 180 | 180 | 20 | 180 |

TABLE I-continued

| Composition | Line | | | | | | | |
|---|---|---|---|---|---|---|---|---|
| | 21 | 23 | 24 | 25 | 26 | 29 | 30 | 31 |
| Urea (kg/day) | 50,249 | | 49,998 | | | | | |
| Ammonia (kg/day) | 5,741 | 5,592 | 287 | 371 | 5,963 | 2,721 | 8,162 | 44,154 |
| Carbon dioxide (kg/day) | 3,716 | 3,677 | 215 | 367 | 4,044 | 2,396 | 7,186 | 32,236 |
| Water (kg/day) | 21,447 | 430 | 20,945 | 5,881 | 6,311 | 1,642 | 4,925 | 4,630 |
| Biuret (kg/day) | 176 | | 185 | | | | | |
| Total | 81,329 | 9,699 | 71,630 | 6,619 | 16,318 | 6,759 | 20,273 | 81,020 |
| Temperature (°C.) | 165 | 102 | 110 | 35 | 46 | 100 | 100 | 165 |
| Pressure (kg/cm$^2$G) | 20 | 2 | 2 | 2 | 2 | 20 | 20 | 180 |

The urea solution drawn out from the first separator 3 was first cooled in the heat exchanger 8 to 180° C. and then led to the reducing valve 18.

On the other hand, 26,200 kg/day of steam of 18.8 Kg/cm$^2$G and 10,800 kg/day of steam of 10 Kg/cm$^2$G were supplied through the lines 32 and 40 respectively, while, 3,700 kg/day of steam of 3.5 Kg/cm$^2$G was fed through the line 42. Through the lines 34 and 35, was recovered 34,150 kg/day of steam of 4.0 Kg/cm$^2$G via a steam generation drum (not illustrated).

What is claimed is:

1. A process for synthesizing urea comprising reacting ammonia and carbon dioxide in a molar ratio of 3:1–5:1 and at a urea synthesis pressure of 150–250 Kg/cm$^2$G to form a urea synthesis effluent containing urea, water, unreacted ammonia and unreacted carbon dioxide, subjecting said urea synthesis effluent to a stripping step using gaseous carbon dioxide at a pressure substantially equal to said urea synthesis pressure and at a temperature of 195°–210° C. to separate unreacted ammonia and carbon dioxide therefrom and thereby to obtain a urea solution containing 10–15% by weight of unreacted ammonia, further separating unreacted ammonia and carbon dioxide from the urea solution at a pressure of 10–30 Kg/cm$^2$G and a temperature of 150°–170° C. to obtain a urea solution containing 8% by weight or less of unreacted ammonia, and subjecting the latter urea solution to a separation step of unreacted ammonia and carbon dioxide which step is operated at a pressure lower than the latter pressure of 10–30 Kg/cm$^2$G.

2. The process as claimed in claim 1, wherein the temperature of the urea solution obtained from the stripping step is first adjusted to 180°–195° C. and then subjected to a separation step for separation of unreacted ammonia and unreacted carbon dioxide at a pressure of 10–30 Kg/cm$^2$G and a temperature of 150°–170° C.

3. The process as claimed in claim 2, wherein the temperature of the urea solution obtained from the stripping step is adjusted by stripping carbon dioxide from the same solution under adiabatic conditions or subjecting the same solution to a heat exchange with the urea solution obtained in the separation step for separation of unreacted ammonia and carbon dioxide which separation step is operated at a pressure of 10–30 Kg/cm$^2$G and a temperature of 150°–170° C.

4. The process as claimed in claim 1, wherein the molar ratio of ammonia to carbon dioxide to be reacted is 3.5:1–5.0:1.

5. The process as claimed in claim 1 or 2, wherein the urea solution obtained from the stripping step is treated in a rectification column having a rectification means in an upper portion thereof and a heating means in a lower portion thereof to remove unreacted ammonia and carbon dioxide.

* * * * *